United States Patent [19]

Oguchi et al.

[11] Patent Number: 4,951,097
[45] Date of Patent: Aug. 21, 1990

[54] METHOD AND APPARATUS FOR BONE HISTOMORPHOMETRY

[75] Inventors: Shigeki Oguchi, Tokyo; Yasuhiro Uotani, Koshigaya; Yoshio Hirano, Tokyo, all of Japan

[73] Assignee: Teijin Limited, Osaka, Japan

[21] Appl. No.: 165,058

[22] Filed: Mar. 7, 1988

[30] Foreign Application Priority Data

Mar. 5, 1987 [JP] Japan .................. 62-48840

[51] Int. Cl.⁵ .................. G01J 3/51; G01N 21/64
[52] U.S. Cl. .................. 356/417; 250/459.1; 250/461.1; 356/419; 382/6
[58] Field of Search ............. 356/317, 381, 417, 402, 356/419; 250/458.1, 459.1, 461.1; 382/6

[56] References Cited

U.S. PATENT DOCUMENTS 3,641,344  2/1972  Markle .................. 250/485.1

Primary Examiner—Vincent P. McGraw
Attorney, Agent, or Firm—Sughrue, Mion, Zinn, Macpeak & Seas

[57] ABSTRACT

A method for bone histomorphometry by using a non-decalcified bone specimen, comprising the steps of: (a) obtaining two pictures A and B by recording different chromatic light transmitted through a same region of said non-decalcified bone specimen or by recording different chromatic fluorescence from the region of said non-decalcified bone specimen; (b) detecting the strength (brightness) $L_{An}$ and $L_{Bn}$ of the corresponding image elements (pixels) An and Bn of said two pictures A and B; (c) determining the ratio $L_{An}/L_{Bn}$; (d) performing the steps (b) and (c) on all corresponding image elements of said two pictures A and B; and (e) with regard to the ratio $L_{An}/L_{Bn}$, calculating and expressing areas of three components of bone, said three components of bone being a calcified bone area, an osteoid area, and a bone marrow area, in said non-decalcified bone specimen.

14 Claims, 2 Drawing Sheets

METHOD AND APPARATUS FOR BONE HISTOMORPHOMETRY

BACKGROUND OF THE INVENTION

1. Field of the Invention

The present invention relates to an improved method for bone histomorphometry and an apparatus suitable therefor. More specifically, the present invention relates to a bone histomorphometry method and a bone histomorphometry apparatus capable of evaluating the respective regions of calcified bone, osteoid and bone marrow cavity constituting bone. Such bone histomorphometry is extremely important for grasping the state of disease of bone in metabolic bone diseases such as osteoporosis and osteomalacia and confirming the therapeutical effect of such disease.

2. Description of the Related Art

Bone is always repeating bone absorption and bone formation, and this metabolism cycle of bone is unbalanced in metabolic bone diseases. For example, in senile osteoporosis, the former surpasses the latter, whereby a reduction in bone amount is brought about. On the other hand, in osteomalacia, calcification is obstructed during bone formation, whereby bone formation is stopped at the stage of the bone substrate to increase the bone tissue not calcified, namely osteoid.

Accordingly, diagnosis of the dynamic state of bone in such diseases, namely the balance in the metabolism cycle, becomes important, but there is no efficient method according to the bone histomorphometry in which the test specimen obtained by bone biopsis is measured by microscopic observation. In such a measurement, important indexes may include proportions of bone amount, calcified bone amount, osteoid amount occupied in unit volume of bone (namely unit area in specimen), or surface areas thereof (namely circumferential lengths of the respective regions in specimen) and the like. As the measuring method practiced at present, there have been employed, for example, the hit point method in which microscopic observation is conducted with an eyeglass having a grating-shaped mark, and the points where the gratings cross the respective portions of test specimen are counted with the naked eye, or the semiautomatic method in which the image is traced with a digitizer (i.e., coordinate inputting device), but these methods both require enormous amounts of time and labor and, therefore, even if utilizable in the field of research, they are far from efficient in providing evaluation results for general clinical purposes.

Particularly, generally speaking, bone is not homogeneous, and its form is different even in the same bone specimen depending on the site to be evaluated. For this reason, to enhance the precision and reproducibility of an evaluation, it is necessary to take a large number of measurement sites of, for example, 50 fields of sight, to obtain the evaluation results for the respective sites and obtain an average value thereof. Also, in this sense, it may be said to be indispensable that a further spread of the effective bone form measurement be made to efficiently perform an evaluation at the respective portions.

SUMMARY OF THE INVENTION

Accordingly, an object of the present invention is to provide a method and an evaluation apparatus capable of efficient bone histomorphometry. That is, it is intended to provide a method and an apparatus for rapidly evaluating the occupied proportions of the respective regions of, for example, calcified bone, osteoid and bone marrow cavity and the interface areas of the respective regions.

Other objects and advantages of the present invention will be apparent from the description set forth hereinbelow.

In accordance with the present invention, there is provided a method for bone histomorphometry by using a non-decalcified bone specimen, comprising the steps of:

(a) obtaining two pictures (or spectral images) A and B by recording different chromatic light transmitted through a same region of said non-decalcified bone specimen or by recording differnt chromatic fluorescence from the region of said non-decalcified bone specimen;

(b) detecting the strength (i.e., brightness) $L_{An}$ and $L_{Bn}$ of the corresponding image elements (i.e., pixels) $A_n$ and $B_n$ of said two pictures A and B;

(c) determining the ratio $L_{An}/L_{Bn}$;

(d) performing the steps (b) and (c) on all corresponding image elements of said two pictures A and B; and (e) with regard to the ratio $L_{An}/L_{Bn}$, calculating and expressing areas of three components of bone, said three components of bone being a calcified bone area, an osteoid area, and a bone marrow area, in said non-decalcified bone specimen.

In accordance with the present invention, there is also provided an apparatus for bone histomorphometry comprising:

(a) a means of composing two different monochromatic pictures from the same region of said non-decalcified bone specimen;

(b) a means of detecting a wave strength in each picture element (pixel) of said two pictures;

(c) a means of scanning each picture element (pixel) to compose said two pictures;

(d) a means of recording said two pictures;

(e) a means of calculating the ratio $L_{An}/L_{Bn}$ of said brightnesses $L_{An}$ and $L_{Bn}$ for the corresponding picture elements An and Bn in said two monochromatic pictures A and B;

(f) a means of calculating the calcified area, osteoid area and bone marrow area of said non-decalcified bone specimen; and (g) a means of displaying the result of the step (f).

BRIEF DESCRIPTION OF THE DRAWINGS

The present invention will be better understood from the description set forth below with reference to the drawings in which:

FIG. 2 to FIG. 4 illustrate the cases when the method of the present invention is applied as contrasted thereto, in which, FIGS. 2 and 3 are monochromatic images of the colors of different systems, respectively, and FIG. 4 shows the brightness ratio $L_{An}/L_{Bn}$;

DESCRIPTION OF THE PREFERRED EMBODIMENT

Figure 1:
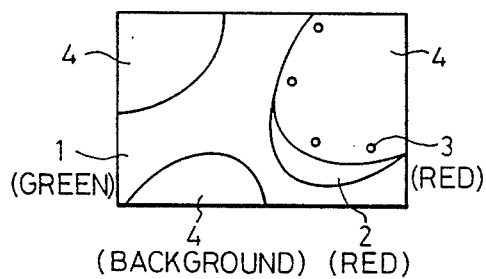
FIG. 1 schematically illustrates the natural light image of the bone specimen obtained by staining according to the Villanuvea Goldner method.

The present inventors have carried out intensive studies in order to accomplish the above-mentioned object, and consequently, found that by obtaining two kinds of spectral images of different color systems for the same region on the field of sight of a microscope of a non-decalcified bone specimen stained as the bone specimen and employing the ratio of brightnesses of the same picture element in both of the spectral images, an image can be reconstituted which can express the respective regions of calcified bone, osteoid and bone marrow cavity of that bone, to accomplish the present invention set forth above.

In the system of the present invention, so long as a monochromatic video camera and an image inputting device are employed, a recognition of calcified bone, osteoid, bone marrow cavity according to the information of light and shade of the image must rely on the light and shade of a non-decalcified bone specimen. However, it is frequently experienced that a mere transfer of a non-decalcified bone specimen to a monochromatic photograph makes such a discrimination very difficult. When staining a Villanuvea, which should be called the standard of a non-decalcified bone specimen (hereinafter sometimes called merely "bone specimen"), the different in light and shade between bone tissue and bone marrow cavity is extremely small, and it is not possible to easily discriminate that those with a higher brightness are bone marrow cavities, while those with a lower brightness are bone tissues, and this cannot be improved even by performing further contrast strengthening as practiced in conventional image treatment. This may be an adverse effect of too objective a judgement with a machine. In observation with the naked eye, even if an error occurs in the thickness of specimen or a variance in light and shade depending on, for example, the staining technique, bone tissue can be discriminated from bone marrow cavity by a subjective judgement of connection between, for example, Figures.

On the other hand, for an efficient evaluation of a bone specimen, the hit point method based on judgement with the naked eye or the semi-automatic method using a digitizer is not suitable, and it is important to use the recognition method based on the information concerning light and shade of a monochromatic image. Thus, the present invention relates to bone histomorphometry on the basis of the information of light and shade of a monochromatic image concerning bone specimen without requiring a judgement by the naked eye.

As the bone specimen of the present invention, it is preferable to use those which exhibit two kinds of color systems of the three kinds of color systems of red, green and blue in the two kinds of regions of the three kinds of regions of calcified bone, osteoid and bone marrow cavity, with the remainder of the above three regions exhibiting the color of the system different from such two kinds of color systems or colorless system (or background), in the natural light (i.e., polychromatic light) image formed by the transmitted light when natural light is irradiated or the fluorescent image obtained when UV-rays are irradiated. The kind of bone to be evaluated according to the present invention is not particularly limited.

The staining method for obtaining such non-decalcified bone specimen is not particularly limited, but a preferred example may be the Villanuvea Goldner method. This method stains osteoid differently from calcified bone, and a sliced strip with a thickness of 10 µm or less is preferred as the bone specimen to be used. The natural light image of the bone specimen obtained is red for osteoid, green for calcified bone, and colorless for bone marrow cavity.

Also, as another example of the bone specimen suitable for the present invention, there may be included the case using the Villanuvea method in which the fluorescent image thereof is employed. More specifically, when UV-rays are irradiated on the bone specimen obtained by use of such a staining method, the fluorescent image obtained is red for osteoid, green for calcified bone, and black for bone marrow cavity. The natural light image of this bone specimen can be used with difficulty as a preferred embodiment of the present invention as mentioned above.

The present invention is characterized by obtaining spectral images of two different kinds of color systems in the same region from such a non-decalcified bone specimen, determining the ratio $L_{An}/L_{Bn}$ of brightnesses $L_{An}$ and $L_{Bn}$ in the picture elements corresponding to the both spectral images, and expressing the bone form on the basis of the value of the ratio $L_{An}/L_{Bn}$.

Figure 2:
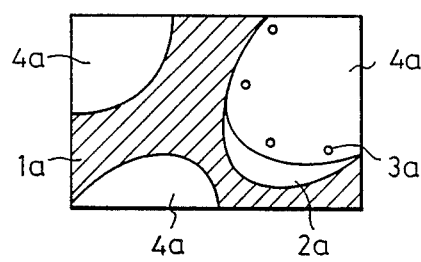
Figure 3:
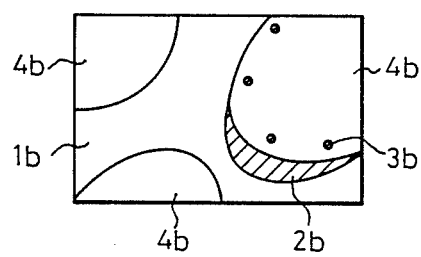
Figure 4:
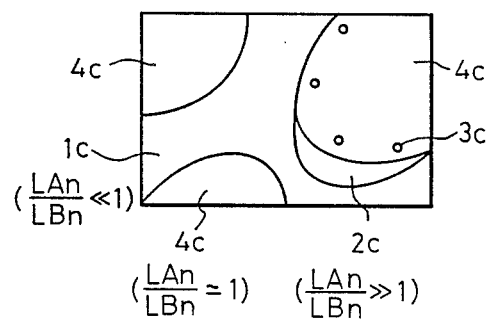

For example, while the bone specimen obtained by staining according to the Villanuvea Goldner method, in its natural light image exhibits green in the region 1 of calcified bone, red in the region 2 of osteoid and the region 3 of cell components and no color in the region 4 of bone marrow cavity, as shown in FIG. 1, natural light or light approximate thereto, namely substantial natural light is transmitted through a spectral filter capable of absorbing lights of colors other than the red system and then transmitted through the bone specimen to obtain a first monochromatic image, and further, the substantial natural light is transmitted through a spectral filter capable of absorbing lights other than the green system and then transmitted through the bond specimen to obtain a second monochromatic image. In such a first image, as shown in FIG. 2, the region 2a of osteoid, the region 4a of bone marrow cavity, and the region 3a of cell components are light, and the region 1a of calcified bone is dark, while in the second image, as shown in FIG. 3, the region 1b of calcified bone and the region 4b of bone marrow cavity are light, and the region 2b of osteoid and the region 3b of cell components are dark. Accordingly, by using both images, when the ratio $L_{An}/L_{Bn}$ of the brightness $L_A$ of the first image to the brightness $L_{Bn}$ of the second image concerning corresponding image elements is taken, as shown in FIG. 4, an extremely great value as compared with 1 is exhibited in the region 2c of osteoid, a value approximate to 1 is exhibited in the region 4c of bone marrow cavity, and a value extremely smaller than 1 is taken in the region 1c of calcified bone. Concerning cell components, since they do not generally exist in large amounts, they may be substantially neglected in an evaluation of bone form according to the method of the present invention, and even if present in small amounts, they can be considered as included within the range of evaluation error. However, for a bone specimen with particularly many cell components, it is effective for enhancement of the evaluation precision to exclude (cut out the image) that proportion from the subsequent operation with a coordinate inputting device before determining the ratio of lightness.

By thus using the ratio $L_{An}/L_{Bn}$ of the respective spectral images of the two different kinds of color systems, the three regions of calcified bone, osteoid and bone marrow cavity can be represented as discriminated from one another with numerical values which are so far apart from one another that they are not influenced by a variance in lightness due to a thickness of the specimen or inhomogeneity of the staining. Thus, according to the present invention, based on light and shade of a monochromatic image can be treated mechanically with ease, as the information concerning bone specimen, calcified bone, osteoid and bone marrow cavity can be expressed with an extremely high contrast as mere values suitable for information processing.

As a specific preferable method for obtaining the two kinds of spectral images of the present invention, the method using of two kinds of spectral filters as mentioned above can be utilized. Such spectral filters may be used at the position of either between a light source and a bone specimen or between a specimen and a light-receiving element with, for example, an enlarging lens provided therebetween. In other words, the light after being transmitted through a bone specimen may be transmitted separately through two kinds of spectral filters to obtain two kinds of monochromatic images.

Also, as another example of the method for obtaining two kinds of spectral images, the method, in which the light for forming the fluorescent image obtained by irradiation of UV-ray on a bone specimen is transmitted separately through two kinds of spectral filters to thereby obtain two kinds of monochromatic images, can be utilized. Further, more specifically, there is the method using a fluorescent microscope, and the position of the spectral filter in this case may be at any position between the bone specimen and the light-receiving element.

Thus, in the method using spectral filter, it is important for enhancing the contrast of the respective regions when expressed in the ratio $L_{An}/L_{Bn}$ to use two kinds of spectral filters each capable of only one system of either two kinds of light of red, green and blue exhibited in natural light image or fluorescent image by calcified bone, osteoid and bone marrow cavity of the bone specimen.

Further, as an alternative method for obtaining two kinds of spectral images in the present invention, the light of the natural light image obtained by transmitting natural light through a bone specimen or the fluorescent image obtained by irradiation of UV-ray on the bone specimen may be subjected to spectroscopy by transmission through a prism means to obtain the monochromatic images of either two kinds of color systems of red, green and blue. The position of such prism means may be between the bone specimen and the light-receiving element, generally after formation of an enlarged natural light image or fluorescent image for obtaining advantageously stable monochromatic images. As a preferable specific example of prism means, one housed in an RGB camera may be included.

In the method of the present invention, a microscope or fluorescent microscope is used for obtaining enlarged images, and a monochromatic video camera or an RGB video camera may be used practically advantageously. Further, as the method for determining the lightness ratio $L_{An}/L_{Bn}$ and expressing the bone histomorphometry with said ratio as the standard, it is effective when obtaining an efficient bone histomorphometry to use a computer system provided with a memory means and an operation processing means.

Thus, according to the bone histomorphometry of the present invention, by expressing the respective regions of calcified bone, osteoid and bone marrow cavity with the value of brightness ratio $L_{An}/L_{Bn}$ as the standard, the respective regions can be discriminated with extremely high contrast as compared with conventional monochromatic image, and the area proportions occupied by the respective regions and further the lengths of the boundary lines can be determined with a high precision and reproducibility and with an extremely good efficiency according to the method of binary-value which is one of the image processing techniques and the method of boundary line representation. Particularly, this method is excellent in that an extremely stable evaluation result can be obtained without substantial influence from variance in a staining degree during preparation of the bone specimen.

Also, even when evaluation is performed by using a bone specimen labelled with tetracycline, bone histomorphometry can be done efficiently by using the evaluation method of the present invention. More specifically, when UV-rays are irradiated on a bone specimen obtained by staining of a bone test sample labelled with tetracycline according to the Villanuvea method, a fluorescent image with the calcified bone being green, the osteoid being red, the bone marrow cavity being black and the labelled portion with tetracycline being yellow is obtained. When such a fluorescent image is received by an RBG camera, the brightness $L_{An}$ in the image of red system becomes low in the region of calcified bone, medium at the labelling portion and high at osteoid, while the brightness $L_{Bn}$ in the image of a red system becomes high in the calcified bone, medium at the labelling portion and low at osteoid, whereby the lightness ratios $L_{An}/L_{Bn}$ taken in the respective regions are extremely smaller than 1 in calcified bone, approximately equal to 1 in the labelling portion and extremely greater than 1 in osteoid. For the region of bone marrow cavity, lightness is extremely small in both images, and the variance becomes great, if the ratio of both is taken. Therefore, it is preferable to make the lightness of image element at a certain level or lower in both of the two images zero, and discriminate its region from other regions by adding the program for setting $L_{An}/L_{Bn}$ to the operation processing step when both the numerator and denominator are zero in determining the ratio of $L_{An}/L_{Bn}$. Thus, also the portion labelled with tetracycline can be expressed as discriminated from other regions with a high contrast by representation of the lightness ratio $L_{An}/L_{Bn}$.

The labelled portion has a shape generally of a curve with a width, but this portion can be easily represented according to the method of a fine line formation. In this way, an automatic measurement, for example, measurement of the average of the distances between, for example, the two labelled lines can be easily carried out.

The bone histomorphometry device of the present invention is suitable for practicing the evaluation method as described above, and is characterized by having an image forming means for obtaining two different kinds of spectral images of different color systems for a non-decalcified bone specimen, a light-receiving means for light-receiving the spectral images, a means of temporarily memorizing the two kinds of spectral images received and an operation processing means for calculating the ratio $L_{An}/L_{Bn}$ of the corresponding picture elements in the two kinds of spectral images memorized and expressing the three kinds of regions of calcified bone, osteoid and bone marrow cavity of the bone specimen with said ratio $L_{An}/L_{Bn}$ as the standard.

Figure 5:
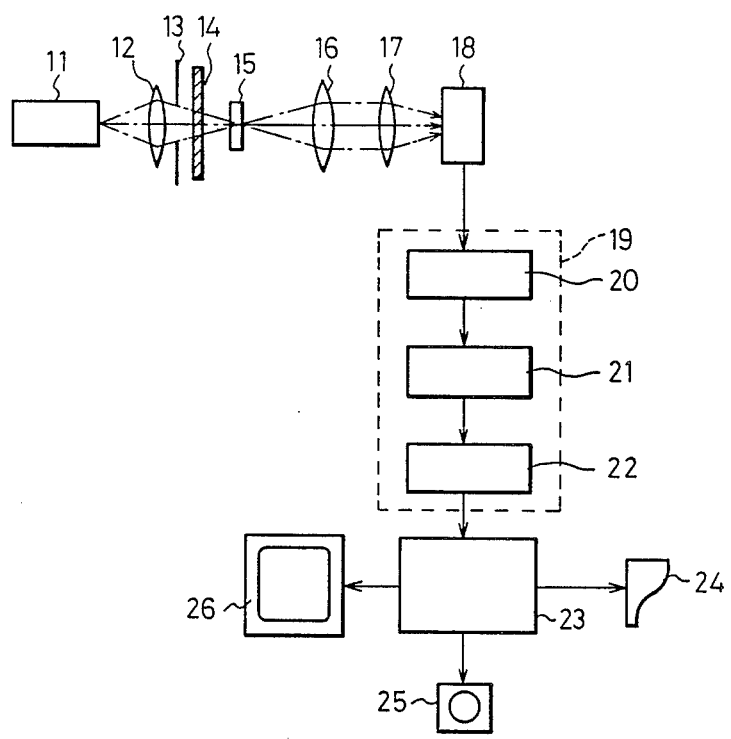
FIG. 5 schematically illustrating a preferred embodiment of the bone form evaluating apparatus in the present invention.

A preferable example of the preferred embodiments is shown in FIG. 5. More specifically, light is condensed through a condensing lens 12 from a light source 11 emitting natural light and, after passing through an iris 13 and a spectral filter 14, is transmitted through a bone specimen 15 to be passed through an objective lens 16 and an eyelens 17 and form an enlarged monochromatic image of the bone specimen, which is received at the light-receiving element means 18. The monochromatic image thus obtained can be temporarily memorized as the brightness $L_{An}$ with a memory means 19 provided with an A/D converter 20, an interface 21 and a frame memory 22. Also, for the same bone specimen, if the spectral filter 14 is exchanged for a spectral filter capable of passing only the light of a different system, another monochromatic image can be similarly memorized as the brightness $L_{Bn}$ with the memory means 19. Further, the apparatus should have the functions of calculating the brightness ratio $L_{An}/L_{Bn}$ for each picture element by using the brightnesses $L_{An}$, $L_{Bn}$ of the two kinds of monochromatic images, determining the respective area proportions of the three kinds of regions of calcified bone, osteoid and bone marrow cavity with the numerical value of the ratio $L_{An}/L_{Bn}$ for each picture element, lengths of the boundary lines of the respective regions and the like and memorizing same. Further, preferably the apparatus also has the function of determining and memorizing the respective numerical values obtained by the same processing for a large number of measuring points at various measuring sites of the bone specimen, determining average values of area ratio of calcified bone and osteoid and the like and boundary line length, and sometimes, performing statistical treatment such as standard deviations thereof. Such an operation processing means 23 can be more readily used in practical application if provided with an image display means 26 for displaying the image of the ratio $L_{An}/L_{Bn}$ standard or the evaluation results thereof, a disc type magnetic recording means 25 and a printing means 24.

In FIG. 5, it is practical to use a microscope from the light source 11 to the eyelens 17, and a monochromatic video camera for the light-receiving element means 18. The spectral filter 14 in FIG. 5 may be at any desired position between the light source 11 and the light-receiving element means.

As other preferable embodiments of the image forming means in the apparatus of the present invention, there may be included fluorescent microscopes comprised of a light source, condensing device, heat ray removing filter and UV-rays transmitting filter, in which two kinds of spectral filters can be used exchangeably between the bone specimen and the light-receiving element means.

Also, in these embodiments, instead of using spectral filters, prism means such as an RGB video camera, etc., can be used for the light-receiving element means to enable a take-out of monochromatic images of either two kinds of systems of red, green and blue. These are also effective embodiments of the apparatus of the present invention.

As explained above, according to the present invention, the occupied ratios of the respective regions of calcified bone, osteoid and bone marrow cavity constituting bone and interface areas of the respective regions and the like, can be determined rapidly and with a high precision, whereby it is possible to conduct very efficient bone histomorphometry.

Also, the present invention is effective in grasping the extent of progress of metabolic bone diseases such as osteoporosis and osteomalacia, and is efficient in confirming the therapeutical effect of such disease.

We claim:

1. A method for bone histomorphometry by using a non-decalcified bone specimen, comprising the steps of:
   (a) obtaining two pictures A and B by recording different chromatic light transmitted through a same region of said non-decalcified bone specimen or by recording different chromatic fluorescence from the region of said non-decalcified bone specimen;
   (b) detecting the strength $L_{An}$ and $L_{Bn}$ of the corresponding image elements $A_n$ and $B_n$ of said two pictures A and B;
   (c) determining the ratio $L_{An}/L_{Bn}$;
   (d) performing the steps (b) and (c) on all corresponding image elements of said two pictures A and B; and
   (e) with regard to the ratio $L_{An}/L_{Bn}$, calculating and expressing areas of three components of bone, said three components of bone being a calcified bone area, an osteoid area, and a bone marrow area, in said non-calcified bone specimen.

2. A method as claimed in claim 1, wherein said non-decalcified bone specimen exhibits said calcified bone area, osteoid area, and bone marrow area by independent chromatic staining or fluorescence.

3. A method as claimed in claim 1, wherein said two pictures A and B are obtained by:
   (a) forming a monochromatic image obtained by transmitting polychromatic light through said non-decalcified bone specimen and a spectral filter capable of transmitting a monochromatic wave length,
   (b) detecting the strength of the transmitted wave of each image element,
   (c) scanning and composing picture A, and
   (d) again performing the processes (a) to (c) at the same region of said non-decalcified bone specimen, transmitting the same wavelengths of polychromatic light through the specimen, but using a different spectral filter capable of transmitting a different monochromatic wave length and composing picture B.

4. A method as claimed in claim 3, wherein the two monochromatic pictures A and B are obtained by transmission of two different monochromatic wavelengths of light.

5. A method as claimed in claim 3, wherein the two monochromatic pictures A and B are obtained by an RGB color video camera.

6. A method as claimed in claim 1, wherein said two pictures A and B are obtained by:
   (a) forming a monochromatic image obtained by transmitting fluorescence generated by irradiating ultra-violet rays onto said non-decalcified bone specimen through a spectral filter capable of transmitting a monochromatic wave length,
   (b) detecting the strength of the transmitted wave of each image element,
   (c) scanning and composing picture A, and
   (d) again performing the processes (a) to (c) at the same region of said non-decalcified bone specimen, transmitting the same wavelengths of ultra-violet rays through the specimen, but using a different spectral filter capable of transmitting a different monochromatic wave length and composing picture B.

7. A method as claimed in claim 6, wherein the two monochromatic pictures A and B are obtained by transmission of two different monochromatic wavelengths of light.

8. A method as claimed in claim 6, wherein the two monochromatic pictures A and B are obtained by an RGB color video camera.

9. An apparatus for bone histomorphometry comprising:
(a) a means of composing two different monochromatic pictures from the same region of said non-decalcified bone specimen;
(b) a means of detecting a wave strength in each picture element (pixel) of said two pictures;
(c) a means of scanning each picture element (pixel) to compose said two pictures;
(d) a means of recording said two pictures;
(e) a means of calculating the ratio $L_{An}/L_{Bn}$ of said brightnesses $L_{An}$ and $L_{Bn}$ for the corresponding picture elements An and Bn in said two monochromatic pictures A and B;
(f) a means of calculating the calcified area, osteoid area and bone marrow area of said non-decalcified bone specimen; and
(g) a means of displaying the result of the step (f).

10. An apparatus as claimed in claim 9, wherein said means of composing two different monochromatic pictures is provided by inserting alternately two different spectral filters capable of transmitting a monochromatic wave length into the light pathway from a polychromatic light source.

11. An apparatus as claimed in claim 10, wherein the polychromatic light source is replaced by an ultraviolet light source to generate fluorescence.

12. An apparatus as claimed in claim 9, wherein said means of composing two different monochromatic pictures is provided by transmitting alternately two kinds of monochromatic light.

13. An apparatus as claimed in claim 9, wherein said means of composing two different monochromatic pictures is provided by an RGB color video camera and a polychromatic light source.

14. An apparatus as claimed in claim 9, wherein said means of composing two different monochromatic pictures is provided by an RGM color video camera and an ultra-violet light source.

* * * * *